US010054591B2

(12) United States Patent
Yarmush et al.

(10) Patent No.: US 10,054,591 B2
(45) Date of Patent: Aug. 21, 2018

(54) AMPLIFYING RARE CELL SURFACE MARKERS

(71) Applicant: The General Hospital Corporation, Boston, MA (US)

(72) Inventors: Martin L. Yarmush, Newton, MA (US); Tali Konry, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 58 days.

(21) Appl. No.: 14/982,458

(22) Filed: Dec. 29, 2015

(65) Prior Publication Data

US 2016/0116479 A1 Apr. 28, 2016

Related U.S. Application Data

(62) Division of application No. 13/583,478, filed as application No. PCT/US2011/027926 on Mar. 10, 2011, now abandoned.

(60) Provisional application No. 61/313,667, filed on Mar. 12, 2010.

(51) Int. Cl.
| | |
|---|---|
| *C12P 19/34* | (2006.01) |
| *G01N 33/574* | (2006.01) |
| *C12Q 1/6804* | (2018.01) |
| *G01N 15/14* | (2006.01) |
| *G01N 15/00* | (2006.01) |

(52) U.S. Cl.
CPC ..... *G01N 33/57492* (2013.01); *C12Q 1/6804* (2013.01); *G01N 15/1484* (2013.01); *G01N 2015/0065* (2013.01); *G01N 2015/149* (2013.01); *G01N 2333/705* (2013.01); *G01N 2458/10* (2013.01)

(58) Field of Classification Search
CPC ............ C12Q 1/6804; C12Q 2531/125; G01N 15/1484; G01N 2015/149; G01N 2458/10; G01N 33/57492; G01N 2015/0065
USPC ....................................................... 435/91.2
See application file for complete search history.

(56) References Cited

U.S. PATENT DOCUMENTS

| | | |
|---|---|---|
| 2004/0152212 A1 | 8/2004 | Huang et al. |
| 2006/0051329 A1 | 3/2006 | Lee et al. |
| 2008/0014589 A1 | 1/2008 | Link et al. |
| 2010/0286290 A1 | 11/2010 | Lohmann et al. |
| 2013/0209988 A1* | 8/2013 | Barber .............. B01L 3/502753 435/5 |

OTHER PUBLICATIONS

Jarvius et al., "In Situ Detection of Phosphorylated Platelet derived Growth Factor Receptor Using a Generalized Proximity Ligation Method," Molecular & Cellular Proteomics, Sep. 2007, 6(9):1500-1509.
Konry et al., "Ultrasensitive Detection of Low-Abundance Surface-Marker Protein using Isothermal Rolling Circle Amplification in Microfluidic Nano-Liter Platform," Small, Feb. 2011, 7(3):1-10.
Brouzes et al., "Droplet microfluidic technology for single-cell high-throughput screening," PNAS 106(34): 14195-14200 (2009).
International Search Report and Written Opinion dated Nov. 30, 2011 issued in International Application No. PCT/US2011/027926, 10 pgs.
Jarvius et al., "In Situ Detection of Phospholylated Platelet derived Growth Factor Receptor Using a Generalized Proximity Ligation Method," Molecular & Cellular Proteomics 6.9 1500-1509 (2007).
Joenssen et al., "Detection and Analysis of Low-Abundance Cell-Surface Biomarkers Using Enzymatic Amplification in Microfluidic Droplets," Angew. Chem. Int. Ed. 48: 2518-2521 (2009).
Konry et al., "Ultrasensitive Detection of Low-Abundance Surface-Marker Protein using sothermal Rolling Circle Amplification in Microfluidic Nano-Liter Platform," NIH Public Access, Author manuscript; available in PMC Jun. 27, 2012, 10 pgs.
Konry et al., "A microsphere-based rolling circle amplification microarray for the detection of DNA and proteins in a single assay," Anal Chem. Jul. 15, 2009; 81(14): 5777-5782.
Non-Final Office Action issued in U.S. Appl. No. 13/583,478 dated Aug. 1, 2013 (5 pages).
Final Office Action issued in U.S. Appl. No. 13/583,478 dated Apr. 15, 2014 (8 pages).
Non-Final Office Action issued in U.S. Appl. No. 13/583,478 dated Jun. 30, 2015 (5 pages).

* cited by examiner

*Primary Examiner* — Cynthia B Wilder
(74) *Attorney, Agent, or Firm* — Fish & Richardson P.C.

(57) ABSTRACT

This invention relates generally to a microfluidic device for encapsulation, incubation, and analysis of cell surface markers or secreted molecules from a single cell.

8 Claims, 3 Drawing Sheets

Figure 3A         Figure 3B         Figure 3C         Figure 3D
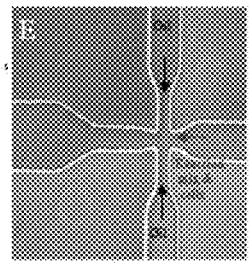 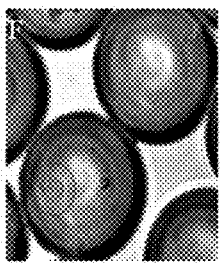 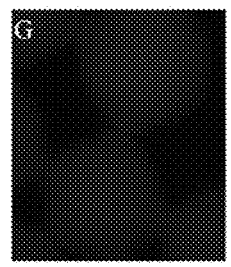 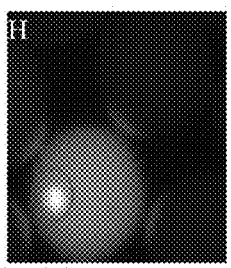
Figure 4
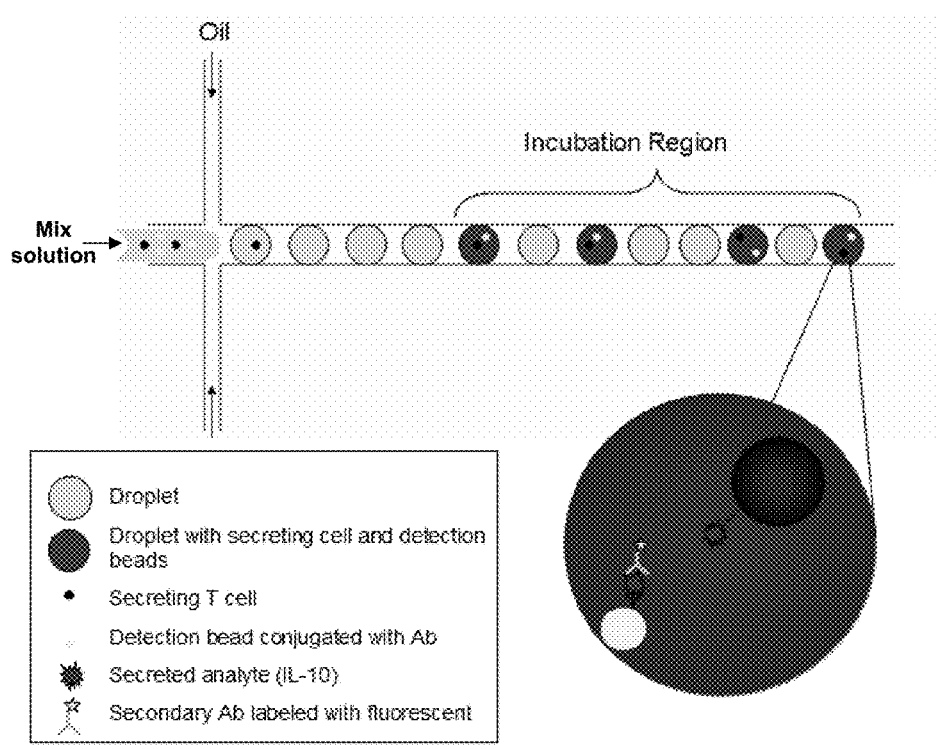

Figure 5A
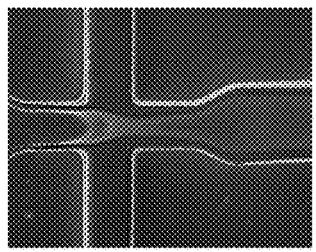
Figure 5B
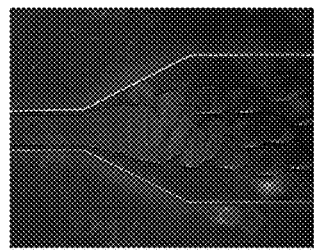
Figure 5C
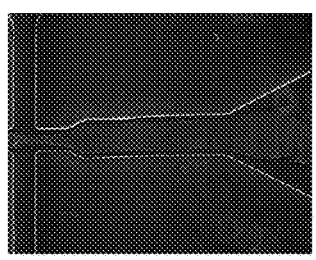
Figure 5D
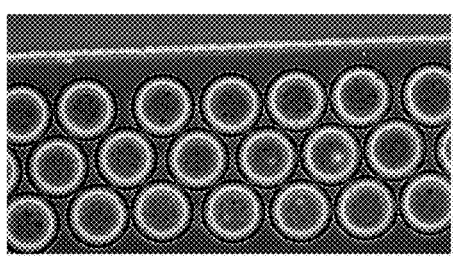
Figure 6A
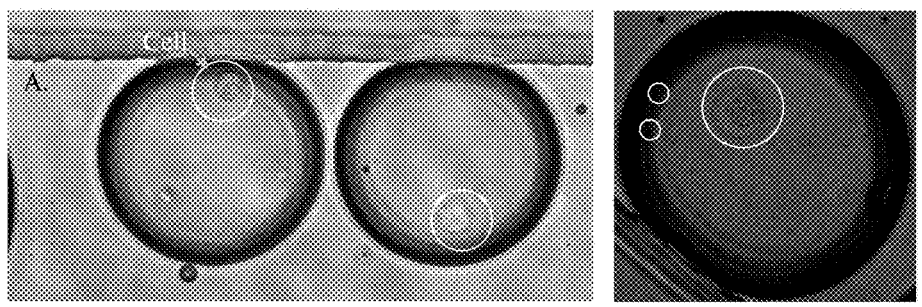
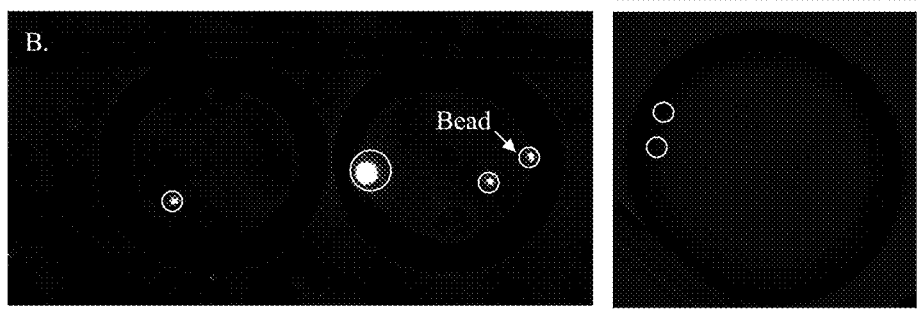
Figure 6B

AMPLIFYING RARE CELL SURFACE MARKERS

CROSS-REFERENCE TO RELATED APPLICATIONS

This application is a divisional of U.S. patent application Ser. No. 13/583,478, filed on Sep. 7, 2012, which is a U.S. National Phase Application under 35 U.S.C. § 371 of International Application No. PCT/US2011/027926, filed on Mar. 10, 2011, which claims the benefit of U.S. Provisional Patent Application No. 61/313,667, filed on Mar. 12, 2010, the contents of which are hereby incorporated by reference in their entireties.

TECHNICAL FIELD

The invention relates to systems and methods for detecting molecules secreted from a single cell and rare cell surface markers, in particular, systems and methods using rolling circle amplification with microfluidic devices for encapsulation, incubation, and analysis of cell surface markers or secreted molecules from a single cell.

BACKGROUND

The ability to gather statistical information over large populations of cells using flow cytometry of cells labeled with fluorescent probes has contributed tremendously to the diagnostics and study of cellular function. In a flow cytometer or a fluorescence-activated cell sorter (FACS), cells are interrogated by flowing them past a detector in a continuous stream of buffer and sorted by molecules either confined within the cells or bound to the cell surface, rather than by properties of the molecules the cells secrete (Köster et al., Lab on a Chip 8, 1110-1115 (2008); Herzenberg et al., Clin. Chem. 48, 1819-1827 (2002); Carroll and Al-Rubeai, Expert Opin. Biol. Ther. 4:1821-1829 (2004)). Low expression of a target molecule can lead to an insufficient or low-intensity detection signal. Further, to sort cells based on secreted molecules, additional tests are usually performed by enzyme-linked immunosorbent assay (ELISA) or comparable methods to verify secretion of a particular molecule of interest from a population of cells rather than from an individual cell. It is also challenging to determine time-dependent variability of secretion from single cells by current methods.

SUMMARY

The present invention is based, at least in part, on systems and methods for amplifying rare cell surface markers, in particular, systems and method using rolling circle amplification with microfluidic devices for encapsulation, incubation, and analysis of cell surface markers or secreted molecules from a single cell. The methods and systems described below can provide high efficiency techniques for specific detection and amplification of cell specific surface markers. The identification of cell surface antigens can be critical to the development of new diagnostic and therapeutic modalities for the management of diseases such as, for example, cancer.

The systems and methods disclosed label cell surface specific markers using rolling circle amplification technique (RCA). RCA is a simple amplification method with high sensitivity and specificity owing to the DNA stringent strand matching requirement and its high signal amplification efficiency (see e.g., Konry et al., Analytical Chemistry 81(14), 5777-5782 (2009); Demidov, Expert Rev. Mol. Diagn., 2(6), 89-95, (2002); and Landegren et al., Comp. Funct. Genomics, 4, 525-530, (2003)). RCA technology detects and measures proteins as well as nucleic acids with unprecedented sensitivity and expanded multiplexing capabilities. A cell specific surface marker is a molecule usually found on the plasma membrane of a specific cell type or limited number of cell types. These markers can be extremely useful to distinguish diseased cells or tissues from those in normal state. The presented technique can be applied to identify, detect, and quantify specific types of cells in complex multi-cellular systems fixed on a glass slide, biochip platform or in flow cytometry analysis.

In one aspect, methods of for detecting cell-surface expression or secretion of a protein or peptide by a single cell include: providing a sample comprising a population of cells and reagents sufficient for detection of a protein or peptide; dividing the sample into subsamples, such that each subsample contains at most one of the population of cells and each subsample is encompassed a hydrophobic fluid; maintaining the subsamples under conditions sufficient to allow detection of the protein or peptide; and detecting the protein or peptide; thereby detecting expression of the protein or peptide by a single cell. Embodiments can include one or more of the following features.

In some embodiments, the protein or peptide is expressed on the surface of the cell or secreted from the cell.

In some embodiments, the reagents comprises rolling circle amplification reagents, e.g., phi29 DNA polymerase, and circular DNA template.

In some embodiments, the reagents comprise antibodies, e.g., antibodies that bind specifically to the protein or peptide.

In some embodiments, the method further comprises sorting the cells based on expression of the protein or peptide. In some cases, wherein sorting the cells comprises using a Fluorescence Activated Cell Sorter (FACS).

In some embodiments, dividing the sample into subsamples comprises combining fluids from multiple inlet channels. In some cases, combining the fluids from multiple inlet channels comprises combining aqueous sample fluid from a first inlet channel with a hydrophobic carrier fluid, e.g., oil, from at least one second inlet channel.

In one aspect, systems for detecting expression of a specific protein or peptide by individual cells of a population of cells include: a fluid control device configured to divide a sample comprising the population of cells into subsamples, such that each subsample contains at most one of the population of cells and each subsample is encompassed a hydrophobic fluid; rolling circle amplification reagents for detection of the presence of the specific protein or peptide; and a device operable to detect the rolling circle amplification reagents in individual subsamples. Embodiments can include one or more of the following features.

In some embodiments, systems also include a cell sorting mechanism operable to sort the subsamples based on measurement of an indicator parameter in each subsample. In some cases, the cell sorting mechanism comprises a fluorescence activated cell sorting mechanism.

In one aspect, a kit includes: a fluid control device configured to divide a sample comprising the population of cells into subsamples, such that each subsample contains at most one of the population of cells and each subsample is encompassed a hydrophobic fluid; and rolling circle amplification reagents for detection of the presence of the specific protein or peptide. Embodiments can include one or more of the following features.

In some embodiments, kits also include a device operable to detect the rolling circle amplification reagents in individual subsamples. In some cases, kits also include a cell sorting mechanism operable to sort the subsamples based on measurement of an indicator parameter in each subsample. For example, the cell sorting mechanism can include a fluorescence activated cell sorting mechanism.

Unless otherwise defined, all technical terms used herein have the same meaning as commonly understood by one of ordinary skill in the art to which this invention belongs. Methods and materials are described herein for use in the specific systems and methods; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

We have demonstrated real time RCA of cancer cell surface specific markers in a microfluidic format. A microfluidic system was used to encapsulate single cells in monodisperse pico-liter RCA reaction droplets. Inclusion of fluorescent probes in the RCA reaction mix permitted the amplification process to be monitored within individual droplets. The resulting fluorescent signal can be the basis for microfluidic cell sorting based on a cell surface marker.

A PDMS microfluidic device was used for the production of monodisperse aqueous emulsion droplets with each droplet containing at most a single cell with a RCA reaction mix. This microfluidic system for RCA offers the advantage of a reduction of reaction volumes, and thereby decreases in reagent and sample consumption which can be critical when limited analyte material is available from clinical samples. Since RCA is an isothermal reaction there is no need for thermal cycling that require sophisticated and expensive instrumentation if compared to microfluidic systems for PCR (see e.g., Konry et al., Analytical Chemistry 81(14), 5777-5782 (2009); Demidov, Expert Rev. Mol. Diagn., 2(6), 89-95, (2002); and Landegren et al., Comp. Funct. Genomics, 4, 525-530, (2003)). Additionally, the new technique will potentially, due to the large multiplexing capacity of RCA, the methods described herein enable parallel detection of various markers thus providing a highly multiplex method by using different combinations of spectrally resolvable fluorophores. Such versatility is superior over PCR-based approaches, since multiplex PCR needs optimization for each primer pair used and still has problems with uniformity.

Practical applications for the disclosed amplification labeling methods and systems for cell surface specific markers include, for example, in cancer cell diagnostics. The identification of cell surface antigens is critical to the development of new diagnostic and therapeutic modalities for the management of cancer. EpCAM, or 'Epithelial Cell Adhesion Molecule' is a pan-epithelial differentiation antigen that is expressed on almost all carcinomas. Therefore detection of EpCAM-expressing cells in the sample serves as the first screening test for cancer. In addition, this specific tumor cell marker is one criterion used in circulating tumor cell (CTC) identification. Usually, anti-EpCAM antibody is used to identify the CTCs. Cells that express this specific cancer marker can serve as molecular targets for sensitive and specific detection. However, tumor cells that express low levels of EpCAM may not detected directly by antiEpCAM antibodies due to low signal intensity. Therefore, the described systems and methods can provide the ability to detect differential expression of EpCAM on the cancer cell using RCA signal that can reduce the likelihood that any target cells are missed.

The PDMS microfluidic devices can be used for production of monodisperse aqueous emulsion droplets of picoliter or nanoliter in size in a continuous oil phase to encapsulate each cell in their own microenvironment. In this hydrodynamic system, focusing, the size of a liquid jet can be considerably reduced to achieve faster mixing time. Since the volume of each drop is restricted, molecules secreted by an individual cell can rapidly attain detectable concentrations. Each droplet contains up to one individual cell encapsulated along with detection reagents, such as fluorescently labeled detection antibodies and conjugated microspheres for secreted analyte measurement (depending on the number of cells, some droplets may have no cells, but optimally no droplets will have more than one cell). In some embodiments, secreted analytes bind to microspheres previously conjugated with analyte-specific antibodies and this binding is detected in real time via detection of a fluorescent signal from labeled antibodies also present in the droplets. In the case of no analyte secretion from the cell, the fluorescence diffuses in the droplet and is not localized on the microsphere surface. Because the cells in the droplets remain viable after encapsulation, the cells can be captured based on signals detected, and cultured to produce clonal populations of cells, e.g., using known cell-sorting and culture methods. It is also possible that the same set of droplets could be used overtime to produce multiple copies of single cell dropletsarray at different time points. This method has an advantage in the fabrication process and device handling, which avoids washing and surface modification steps as compared to previously published single cell secretion analysis. In addition, other methods for the analysis of individual cells in large numbers do not allow both high-throughput analysis of a secreted product and recovery of living cells for clonal expansion.

Other features and advantages of the invention will be apparent from the following detailed description and figure, and from the claims.

DESCRIPTION OF DRAWING

FIGS. 3A to 3D are a series of microscope images of PC3 cells fixed on a glass slide.

FIG. 4 is a schematic illustration of experimental setup.

FIGS. 5A to 5C are a series of microscope images of microfluidic devices for encapsulation in created droplets.

FIG. 5D is a photograph of an incubation and analysis channel.

FIGS. 6A and 6B are a series of (A) bright field and (B) fluorescence microscope images of aqueous droplets containing T cells, beads, and fluorescent secondary antibody.

DETAILED DESCRIPTION

The systems and methods described herein are based, at least in part, on the discovery of methods for detecting molecules secreted by single cells and rare cell surface markers. In some embodiments, the methods use rolling circle amplification with microfluidic devices for encapsulation, incubation, and analysis of cell surface markers or secreted molecules from a single cell. Detection of cell surface specific markers in microfluidic format can be utilized in a number of applications, e.g., in cancer cell diagnostics.

Cell Surface Markers

A cell surface marker is a molecule found on the external cell wall or plasma membrane of a specific cell type or a limited number of cell types (see e.g., Molday and Maher, Histochemical Journal 12:273-315 (1980); Hewett, International Journal of Biochemistry & Cell Biology 33:325-335 (2001); and Pembrey et al., Applied and Environmental Microbiology 65:2877-2894 (1999)). These markers are of importance in clinical studies and development of new diagnostic and therapeutic modalities for the management of human diseases such as cancer (see e.g., Molday and Maher, Histochemical Journal 12:273-315 (1980); Hewett, International Journal of Biochemistry & Cell Biology 33:325-335 (2001); and Pembrey et al., Applied and Environmental Microbiology 65:2877-2894 (1999)). Various therapeutic strategies could be employed to exploit the selective expression of targets on the surface of tumor-associated cell such as antibody- or gene-directed therapy, and small molecule approaches (Hewett, International Journal of Biochemistry & Cell Biology 33:325-335 (2001)). These therapeutic approaches depend on the identification of suitable selective targets on the associated tumor cell (Hewett, International Journal of Biochemistry & Cell Biology 33:325-335 (2001)). A significant challenge in diagnostic analysis of these targets via immunolabeling is insufficient or low-intensity detection signal due to low expression of the target. This leads to inefficient use of existing antibodies and a need for sensitive signal amplification technique. Therefore, the present methods, which can include use of the RCA technique can be used to enhance the intensity of the signal of the interrogated cell surface marker.

Figure 1:
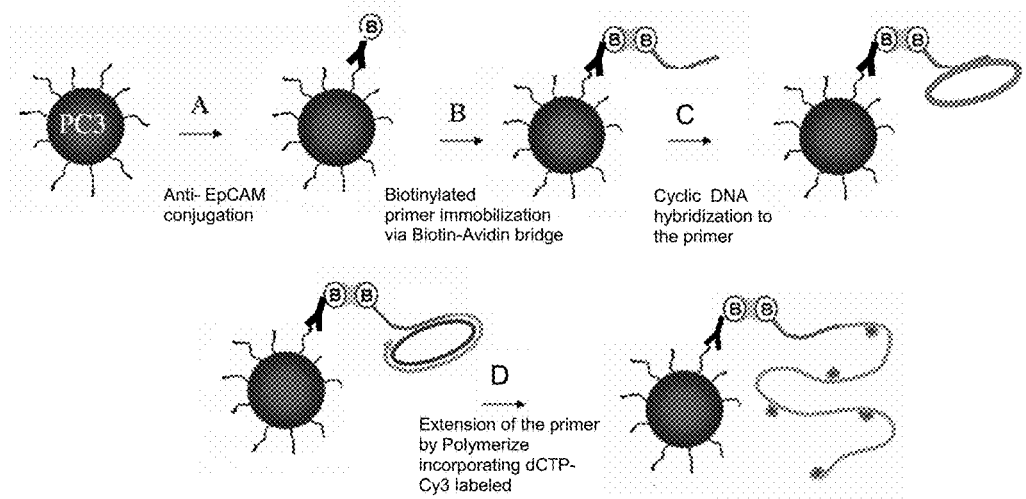
FIG. 1 is a schematic illustration of an RCA assay for the detection of a target surface protein.

FIG. 1 schematically illustrates an exemplary RCA assay for the detection of analytes, e.g., a target surface protein. In this example, anti-EPCAM antibody binds to a target EpCAM protein and is in turn bound by secondary biotin-labeled antibodies (step A). An avidin bridge captures a biotinylated DNA probe (step B). Cyclic DNA is hybridized to the primer (step C), and the capture probe is extended by polymerase (step D).

It will be understood by skilled practitioners that any molecule that is secreted or found on the cell wall or plasma membrane of any cell, e.g., a marker can be detected. For example, cell surface markers that are expressed on a specific cell type or a limited number of cell types can be detected. The process will be described for use with cancer cells, although it may be adapted for use with other cells, e.g., stem cells and immune cells. Examples of cell surface markers include, but are not limited to, membrane proteins such as receptors, transporters, ion channels, proton pumps, and G protein-coupled receptors; extracellular matrix molecules such as adhesion molecules (e.g., integrins, cadherins, selectins, or NCAMS); See, e.g., U.S. Pat. No. 7,556,928, which is incorporated herein by reference in its entirety.

Diagnostic markers for T-cells include the T-cell receptor (TCR) with its associated CD3 signaling complex as well as CD5 and the E-receptor (CD2). The presence of membrane immunoglobulin (mIg), which functions as antigen receptor, is diagnostic for B-cells. Complement receptors (CR) and Fc receptors (FcR) which can mediate opsonization, and MEW Class II molecules which are important in antigen presentation, are present on B-cells and macrophages, as well as dendritic cells. Two major classes of T-cells are distinguished by the presence of either CD4 (on $T_H$ and $T_{reg}$) or CD8 (on $T_C$). $T_H$ cells can be further subdivided into $T_{H1}$ and $T_{H2}$, which produce different cytokines and have distinct physiological roles.

Secreted Molecules

As used herein, secretion is the process of releasing a molecule from a cell, and occurs in prokaryotes and eukaryotes. For example, secretion is an important mechanism in bacterial functioning and operation in their natural surrounding environment for adaptation and survival. Eukaryotic cells have a highly evolved process of secretion, which may involve the classical endoplasmic reticulum (ER)-Golgi pathway. Many mammalian cell types have the ability to be secretory cells and thus have a well developed ER and Golgi apparatus to fulfill this function. Cells in humans that produce secretions include those in the gastrointestinal tract, which secretes digestive enzymes and gastric acid; the lung, which secretes surfactants; sebaceous glands, which secrete sebum to lubricate the skin and hair; the pancreas, which secretes insulin; and meibomian glands in the eyelid, which secrete sebum to lubricate and protect the eye. Further, cells of the immune system can secrete cytokines and proteins.

Secretome analysis can be used e.g., to examine molecules secreted from specific cells, measure time-dependent variability of secretion, and identify unique types of cells that respond to activation with specific analyte secretion. The process will be described for use with IL-10, although it may be adapted for use with other secreted molecules, e.g., proteins, peptides, enzymes, cytokines, chemokines, hormones, toxins, and antimicrobial peptides.

To demonstrate the ability of droplet based single cell secretion analysis, IL-10 secretion was measured from a CD4+CD25+ regulatory T cell clone. IL-10 is an anti-inflammatory cytokine with pleiotropic activities on B, T, and mast cells and is produced by a variety of cell types in response to activation (Pestka et al., Annu Rev Immunol. 22:929-79 (2004)). It has been reported that diminished IL-10 production is associated with autoimmunity (Astier and Hafler, J Neuroimmunol. 191:70-8 (2007)). Thus, since IL-10 can exert its inhibitory activity through multiple effects on different cell types, it is important to understand how its secretion is regulated and to examine the unique cells that respond to IL-10. Understanding how IL-10 secretion is regulated in different cell types would be markedly enhanced by the ability to detect and re-isolate only those viable cells that are actively secreting IL-10 from the majority of cells in the population that are not producing IL-10. The technology described herein can be used to isolate IL-10 secreting cells by encapsulating cells, and later recovering the cells from the drops (e.g., using FACS).

It will be understood by skilled practitioners that this method can also be applied to multitarget detection. Additional individually detectable microspheres that bind other targets can be incorporated in this type of secretion measurement. In this way, a single cell secretome can be achieved using multiple microspheres previously encoded with different capturing antibodies. The ability to use combinations of analytes for signal generation should enables simplification of sorting and detection analysis. For example, since monitoring of CD4+CD25+ regulatory T cells shows promise in cancer immunotherapy, the system can be applied to study new paradigms for designing cytokine antagonists and cell-cell regulation. The encapsulation of two different cells in the same droplet to study the direct interaction between them (with the secretion of a cytokine or the upregulation of a cell surface receptor as output), and screening of different blocking/agonistic antibodies to surface receptors could be some of the various further applications to this system.

Figure 2:
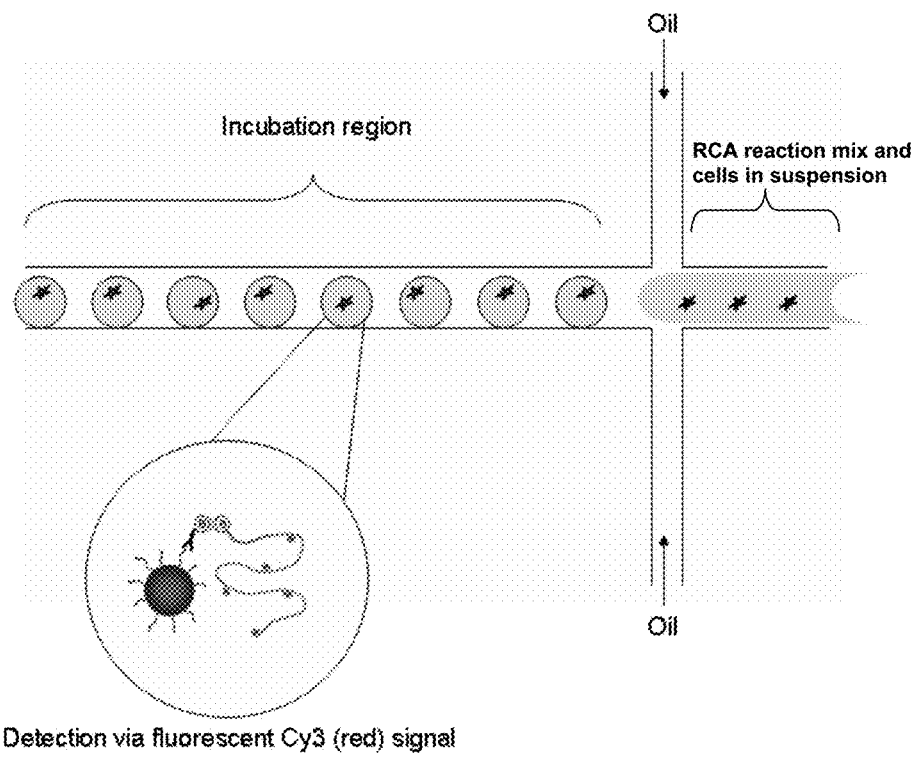
FIG. 2 is a schematic illustration of a microfluidic cell sorting system for RCA in drops.

FIG. 2 is a schematic illustration of a microfluidic cell sorting system for RCA in drops. The microfluidic device produces monodisperse aqueous emulsion droplets containing single cells and an RCA reaction mix. The droplets can then be incubated (e.g., stored in an incubation region of the microfluidic device).

EXAMPLES

The invention is further described in the following examples, which do not limit the scope of the invention described in the claims.

Example 1: RCA Amplification of Epithelial Cell Adhesion Molecule (EpCAM) Using the PC3 Human Prostate Cancer Cell Line EpCAM is a pan-epithelial differentiation antigen that is expressed on almost all carcinomas, therefore detection of EpCAM-expressing cells in a sample can serve as first screening test for cancer (Spizzo et al., Breast Cancer Research and Treatment 86:207-213 (2004)). In addition, this specific tumor cell marker is usually used to identify a circulating tumor cell (CTC) (Nagrath et al., Nature 450: 1235-1238 (2007)). However tumor cells that express a low level of EpCAM may not be detected directly by anti-EpCAM antibodies due to low signal intensity (Deng et al., Breast Cancer Research 10:1-11 (2008)). Therefore the ability to detect differential expression of EpCAM on the cell using a RCA signal can ensure that no target cells are missed.

An RCA signal can be confined locally if the amplification primer is immobilized onto a solid support (Konry et al., Analytical Chemistry 81: 5777-5782 (2009); Smolina et al., Applied and Environmental Microbiology 73:2324-2328 (2007)) and the resulting signal can be detected directly via fluorescent microscopy and/or digitally quantified with a GenePix® microarray scanner (Smolina et al., Applied and Environmental Microbiology 73:2324-2328 (2007)). Two sets of experiments were performed. Representative results obtained in these experiments are presented in FIGS. 3A-3D.

Microscope images of PC3 cells fixed on a glass slide previously labeled with DAPI (blue) were taken. The PC3 cells were labeled directly with biotinylated anti-EpCAM antibodies and Cy3 fluorescent labeled streptavidin. The specificity of the system was also tested by applying the same conditions to lymphocytes. As lymphocyte cells do not express EpCAM, no fluorescent signal was detected using the direct detection method.

In this experiment, PC3 cells were labeled using the RCA technique. In this approach, the cells were first labeled with biotinylated anti-EpCAM antibodies. Biotinylated primers were immobilized via a biotin-avidin bridge to the biotinylated anti-EpCAM antibodies. Next, circular template (padlock) was immobilized to the primers and isothermally amplified by phi29 DNA polymerase. As the amplification is isothermal, the RCA process preserves the integrity of antibody-antigen (EpCAM) complexes. The RCA product contains thousands of repeat sequences that contain fluorescently labeled nucleotides. RCA amplifies the detection signal and allows for the detection of PC3 cancer cells.

Isothermal amplification using phi29 DNA polymerase was also performed in droplets. In order to evaluate the method for screening a single-cell, a drop-based PDMS microfluidic device was applied to encapsulate PC3 cells in distinct picoliter-sized drops of RCA reagents. A PDMS microfluidic system which generates monodisperse droplets in a microchannel through shearing flow at a T-junction or a flow-focusing zone has been previously described (Kiss et al., Anal. Chem. 80:8975-8981 (2008); Köster et al., Lab on a Chip, 8:1110-1115 (2008)). Other methods of generating droplets (e.g., separating the sample into subsamples) could also be used.

The RCA reaction droplets were conveyed by the oil flow through channels in a microfluidic chip. Individual droplets were then focused in the array channel for amplification reaction of cell surface marker and optical interrogation (FIGS. 3A to 3D). An array like channel permits incubation for polymerization and measuring of fluorescence signal in real time from each individual cell, providing information on amplification efficiency within each droplet. The array channel herein permits simultaneous interrogation of multiple droplets/reactions/cells and it can be easily designed to hold thousands of droplets (Kiss et al., Anal. Chem. 80:8975-8981 (2008)). Comparing the fluorescent image of an encapsulated cell in an RCA reaction at the beginning of the incubation (see FIG. 3C) with the cell after 1.5 hours (see FIG. 3D), it is clear that the RCA was performed on a single PC3 cancer cell enclosed in a droplet. In this research setting, real-time RCA in pL-drops can provide quantitative measurements, if fluorescence was recorded using a custom optics system and software similar to one described by Kiss et al. (Anal. Chem. 80:8975-8981 (2008)).

The basic cell encapsulation device uses a flow focusing geometry to produce droplets (Brouzesa et al., Proc. Natl Acad. Sci. USA 106: 14195-14200 (2009); Edd et al., Lab Chip 9:1859-65 (2009); Köster et al., Lab Chip 8:1110-1115 (2008); Wan et al.) FIG. 4 illustrates a PDMS droplet-based microfluidic device. Three inlet channels form a nozzle as their flows combine (see FIGS. 5A and 5B). The center stream contains beads, cell and secondary antibodies suspension while the side streams contain the oil phase. The size of the droplets controlled by matching the size of the nozzle orifice to the drop diameter and operating the device in the dripping regime. For drop formation, the flow rate ratio of water to oil was adjusted to the Qw/Qo=0.5. For single cell studies, all drops should optimally contain at most one cell, so that the majority of drops contain no cell at all since the encapsulation process follows Poisson statistics. Although the number of single-cell-bearing drops is rather low, for these experiments this is not severe, given the high production and screening rate that can be achieved with microfluidic devices.

Microfluidic Device Fabrication

Microfluidic flow chambers were fabricated by soft lithography. Negative photo resist SU-8 2025 or SU-8 2100 (MicroChem, Newton, Mass.) was deposited onto clean silicon wafers to a thickness of 50 lm, and patterned by exposure to UV light through a transparency photomask (CAD/Art Services, Bandon, Oreg.). The Sylgard 184 poly (dimethylsiloxane) (PDMS) (Dow Corning, Midland, Mich.) was mixed with crosslinker (ratio 10:1), poured onto the photoresist patterns, degassed thoroughly and cured for at least 1 hour at 65° C. The PDMS devices were peeled off the wafer and bonded to glass slides after oxygen-plasma activation of both surfaces. To improve the wetting of the channels with mineral oil, the microfluidic channels are treated prior to the experiments with Aquapel (PPG Industries, Pittsburgh, Pa.) by filling the channels with the solution as received and then flushing them with air. Polyethylene tubing with an inner diameter of 0.38 mm and an outer diameter of 1.09 mm (Becton Dickinson, Franklin Lakes, N.J.) connected the channels to the syringes. Syringes were used to load the fluids into the devices, while the flow rates were controlled by syringe pumps. Optimum devices for drop formation and cell encapsulation are 40 lm high with a 35 lm-wide nozzle. To vary the drop size, we also used a channel height of 25 lm and different nozzle widths. The channel for cell incubation are 100 lm high, the 1 width is 500 lm, and the length is 2.88 m. All inlet channels were equipped with patterned filters which prevent dust particles from clogging the channels downstream.

As lymphocyte cells do not express EpCAM, no fluorescent signal was detected using the RCA methods.

CD4+CD25+ High Regulatory T Cell Cloning

Whole mononuclear cells were isolated from human blood drawn from healthy control donors by Ficoll-Hypaque (Amersham Biosciences) gradient centrifugation, and total CD4 T cells were isolated by negative selection using a CD4+ T-cell isolation kit II (Miltenyi Biotec, Bergisch Gladbach, Germany) and stained for fluorescence-activated cell sorting (FACS) with antibodies against CD45RA (HI100), CD25 (M-A251), and HLA-DR (L-243). The specific DR-Treg (CD45RA-CD25highDR-) (Baecher-Allan et al., J Immunol. 176:4622-31 (2006)), and memory T responder (CD45RA-CD25med) populations were sorted in a FACSAria™ cell sorter (BD Biosciences) at one cell per well in XVIVO-15 (Lonza) medium containing 5% human serum and stimulated with soluble anti-CD3 (clone Hit3a, BD Biosciences) and anti-CD28 (clone 28.2) (both at 1 µg/mL), irradiated APCs (105/well), and IL-2 (50 U/mL). Half of the medium was replaced with fresh medium containing IL-2 (50 U/mL) starting at day 10 and every 3 to 4 days thereafter. After 4 weeks of expansion, each clone was tested for FoxP3 expression and IL-10 production.

Preparation of Microsphere Sensors

SPHERO™ Avidin Coated Particles (0.7-0.9 µm) were conjugated with biotinylated IL-10 monoclonal capture antibodies (Invitrogen AHC7109) and suspended in PBS. A microcentrifuge tube containing the mixture was shaken at 25° C. for 4 hours. The microspheres were washed once with 300 µL Tris-Starting Block (blocking buffer) and suspended in 300 µL blocking buffer. The suspension was shaken at 25° C. for 30 minutes and then washed once with 300 µL blocking buffer. The microsphere probes were suspended and stored in 100 µL blocking buffer at 4° C.

A mixed solution of cells, anti-IL-10 conjugated microspheres (1 mg), and rat anti-human IL-10 FITC conjugated antibodies, at a concentration of 1 µg/mL (Invitrogen RHCIL1001) were ejected for encapsulation with a syringe. After encapsulation, the flow in the channels was stopped and the outlet of the device was blocked allowing previously encapsulated droplets to be incubated for 3 hours.

Image Analysis

Fluorescence images were captured on a Zeiss 200 Axiovert microscope using an AxioCAM MRm digital camera. FITC fluorescence (excitation 488 nm, emission 525 nm) was monitored to evaluate the microsphere assay (FIG. 6B).

The method described combines the sensitivity of enhanced RCA detection with a reduction in reaction volumes, reagent, and sample consumption due to the microfluidic format. This system provides high-throughput, specific marker amplification of thousands of reactions per hour combined with real-time monitoring of individual reactions. In addition, various therapeutic strategies such as antibody- or gene-directed therapy, and small molecule approaches, exploiting the selective expression of targets on the surface of tumor-associated cell, could benefit from this sensitive and rapid protein surface detection method. The correlations between surface protein expressions data obtained from a tumor cell before treatment and after the responses of patients to various therapeutic regimens can be obtained on a single cell level. In addition, individual tumor cell analysis, if applied for detection of CTCs, could provide important information, once a cell is recovered from a drop for future testing.

Example 2: Microfluidic Cell Sorting Based on IL-10 Secretion

Single CD4+CD25+ regulatory T cells were encapsulated in distinct nL-sized microenvironment drops and IL-10 secretion was measured in the incubation channel (FIGS. 5D, 6A, and 6B). A detectable concentration of IL-10 secreted by an individual cell was reached in 2 to 3 hours in the restricted volume of droplet (FIGS. 6A and 6B). The droplets with a single cell that produced IL-10 were detected via a fluorescent signal accumulated on the surface of microspheres. FIGS. 6A and 6B depict aqueous droplets containing T cells, beads, and fluorescent secondary antibody after 3 hours incubation in the channel. The microspheres and cells can be seen in the bright field image (FIG. 6A). FIG. 6B (left panel) shows the fluorescence image where secondary fluorescently labeled antibody has been localized on the beads, indicating the secretion of IL-10 from the cell and later binding to the microspheres. FIGS. 6A and 6B (right panels) present an encapsulated T cell which is not secreting IL-10 from the same batch experiment.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of detecting cell-surface expression or secretion of a protein or peptide by individual cells of a population of cells, the method comprising:
providing a sample comprising a population of cells and reagents sufficient for detection of a protein or peptide, wherein the reagents comprise a biotinylated antibody that binds specifically to the protein or peptide, an avidin bridge, a biotinylated DNA probe, a circular DNA template capable of hybridizing with the biotinylated DNA probe, a phi29 polymerase, and a fluorescently-labeled nucleotide;
incubating the sample under conditions such that the biotinylated antibody binds to the protein or peptide, the biotinylated antibody and the biotinylated DNA probe bind to the avidin bridge, the circular DNA template hybridizes with the biotinylated DNA probe, and the phi29 polymerase extends the DNA probe with the fluorescently-labeled nucleotide, thereby fluorescently-labelling the protein or peptide;
dividing the sample into subsamples, such that each subsample contains at most one cell of the population of cells and each subsample is encompassed in a hydrophobic fluid;

maintaining the subsamples under conditions sufficient to allow detection of the fluorescently-labelled protein or peptide; and detecting the fluorescently-labelled protein or peptide in the subsamples;

thereby detecting the cell-surface expression or secretion of the protein or peptide by individual cells of the population of cells.

2. The method of claim 1, wherein the method further comprises sorting the individual cells based on the detection of the fluorescently-labelled protein or peptide.

3. The method of claim 2, wherein sorting the cells comprises using a Fluorescence Activated Cell Sorter (FACS).

4. The method of claim 1, wherein dividing the sample into subsamples comprises combining fluids from multiple inlet channels.

5. The method of claim 4, wherein combining the fluids from multiple inlet channels comprises combining aqueous sample fluid from a first inlet channel with a hydrophobic carrier fluid.

6. The method of claim 1, wherein the cell is a cancer cell, a stem cell, or an immune cell.

7. The method of claim 1, wherein the protein is epithelial cell adhesion molecule (EpCAM).

8. The method of claim 1, wherein the cells are viable cells.

* * * * *